(12) United States Patent
Delaunay et al.

(10) Patent No.: US 9,439,987 B2
(45) Date of Patent: Sep. 13, 2016

(54) DEVICE AND METHOD FOR ULTRA-HIGH TEMPERATURE STERILIZATION OF AN EMULSION

(75) Inventors: Jean-Claude Delaunay, Clermont L'Herault (FR); Franck Legendre, Graulhet (FR)

(73) Assignee: PIERRE FABRE DERMO-COSMETIQUE, Boulogne (FR)

( * ) Notice: Subject to any disclaimer, the term of this patent is extended or adjusted under 35 U.S.C. 154(b) by 183 days.

(21) Appl. No.: 14/232,498

(22) PCT Filed: Jul. 11, 2012

(86) PCT No.: PCT/EP2012/063604
§ 371 (c)(1),
(2), (4) Date: Feb. 10, 2014

(87) PCT Pub. No.: WO2013/007755
PCT Pub. Date: Jan. 17, 2013

(65) Prior Publication Data
US 2014/0138048 A1    May 22, 2014

(30) Foreign Application Priority Data

Jul. 11, 2011 (FR) ...................... 11 56288

(51) Int. Cl.
*A61L 2/04* (2006.01)
*A61L 2/00* (2006.01)
*A61K 8/06* (2006.01)

(52) U.S. Cl.
CPC .................. *A61L 2/04* (2013.01); *A61K 8/064* (2013.01); *A61L 2/0023* (2013.01); *A61K 2800/805* (2013.01)

(58) Field of Classification Search
CPC ........ A61L 2/04; A61L 2/0023; A61K 8/064
See application file for complete search history.

(56) References Cited

U.S. PATENT DOCUMENTS

| 2,217,698 | A | * | 10/1940 | Musher | A23L 1/24 426/576 |
| 5,585,130 | A | * | 12/1996 | Aeschbach | C11B 5/0085 426/541 |
| 5,895,626 | A | * | 4/1999 | Nakata | A23L 3/00 366/208 |
| 6,123,976 | A | * | 9/2000 | Stoddard | A23C 11/103 426/598 |

(Continued)

FOREIGN PATENT DOCUMENTS

| EP | 0524751 A2 | 1/1993 |
| EP | 2032175 B1 | 3/2011 |

(Continued)

*Primary Examiner* — Regina M Yoo
(74) *Attorney, Agent, or Firm* — Im IP Law PLLC; C. Andrew Im

(57) ABSTRACT

A method for high temperature sterilization of an emulsion, in particular a dermocosmetic preparation. The method comprises the steps of gradually pre-heating, performing ultra-high temperature sterilization and gradually cooling the emulsion. The emulsion is heated up to a pre-heating temperature, which is the temperature of the emulsion at the stability limit. Ultra-high temperature sterilization is performed by infusion of the pre-heated emulsion by heating the emulsion up to a sterilization temperature, maintaining the emulsion at the sterilization temperature, and cooling the emulsion under a vacuum at an end-of-sterilization temperature. The emulsion is gradually cooled with agitation to a storage temperature.

8 Claims, 2 Drawing Sheets

(56) References Cited

U.S. PATENT DOCUMENTS

| | | | | |
|---|---|---|---|---|
| 6,596,335 | B1* | 7/2003 | Lo | A23L 1/182 |
| | | | | 426/399 |
| 6,673,311 | B1* | 1/2004 | Sotoyama | A23L 3/0155 |
| | | | | 422/1 |
| 8,603,946 | B2* | 12/2013 | Bernaert | A23C 9/1544 |
| | | | | 504/163 |
| 2002/0164159 | A1 | 11/2002 | De Stoutz | |
| 2003/0099757 | A1* | 5/2003 | Budinoff | A23C 9/1544 |
| | | | | 426/618 |
| 2005/0058762 | A1 | 3/2005 | Kroening | |
| 2005/0255229 | A1* | 11/2005 | Liukko | A23B 7/00 |
| | | | | 426/658 |
| 2006/0286280 | A1* | 12/2006 | Bradford | A21D 2/16 |
| | | | | 426/656 |
| 2008/0160149 | A1* | 7/2008 | Nasrallah | A23L 1/0008 |
| | | | | 426/521 |
| 2009/0148343 | A1 | 6/2009 | Lopez et al. | |
| 2010/0158984 | A1* | 6/2010 | Qvyjt | A61K 9/0095 |
| | | | | 424/439 |
| 2010/0159079 | A1* | 6/2010 | Qvyjt | A23D 9/04 |
| | | | | 426/89 |

FOREIGN PATENT DOCUMENTS

| | | |
|---|---|---|
| JP | 2004105181 A | 4/2004 |
| WO | 2007/148022 A2 | 12/2007 |

* cited by examiner

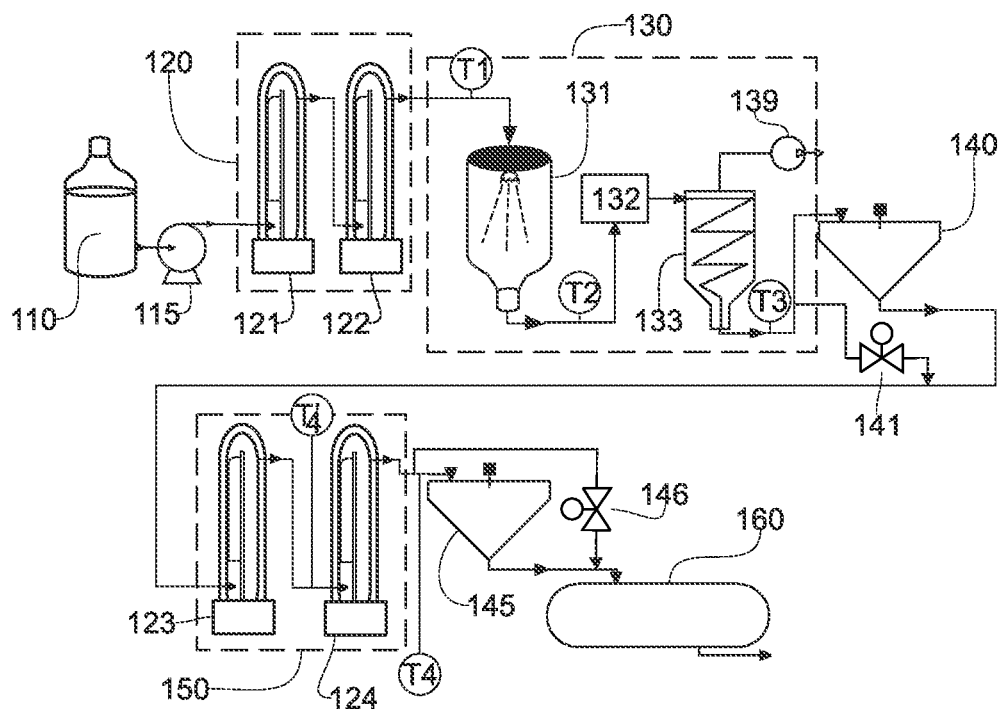
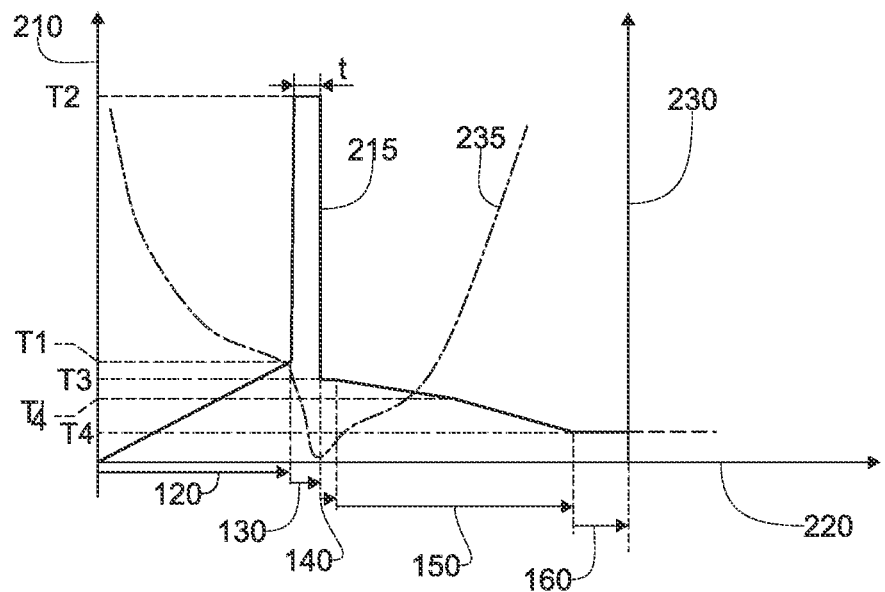
Fig. 1
Fig. 2

DEVICE AND METHOD FOR ULTRA-HIGH TEMPERATURE STERILIZATION OF AN EMULSION

RELATED APPLICATIONS

This application is a §371 application from PCT/EP2012/063604 filed Jul. 11, 2012, which claims priority from French Patent Application No. 11 56288 filed Jul. 11, 2011, each of which is herein incorporated by reference in its entirety.

TECHNICAL FIELD OF THE INVENTION

The invention relates to a device and method for ultra-high temperature sterilization of an emulsion, which is unstable at the sterilization temperature. It is, more specifically but not exclusively, suitable for sterilizing a dermocosmetic preparation in the form of gels, creams or milks. More generally, the invention relates to a product in emulsion or suspension form. Such products comprise at least two immiscible phases; one of the phases, called "internal" or "dispersed" phase, is in suspension and dispersed in the other, called "external" or "continuous" phase. In the products affected by this invention, the internal phase is condensed or liquid and the external phase is liquid.

BACKGROUND OF THE INVENTION

It is possible for such an emulsion to be "broken", i.e. for it to lose its characteristics as an emulsion by various mechanisms such as creaming, flocculation or coalescence. These phenomena, which sometimes lead to the destruction of the emulsion, are particularly sensitive to the size of the particles in suspension and to the viscosity of the external phase. The finer the particles of the internal phase and equally, the more viscous the external phase, the stabler the emulsion will be and vice versa. In a way, the stability is a measurement of the time that said emulsion takes to lose its characteristics as an emulsion.

In many fields, such as cosmetics or pharmaceuticals, products in the form of an emulsion must meet preservation standards in regards of microbial proliferation. One of the methods for ensuring this preservation is to include preservatives in the product, such as esters of 4-Hydroxybenzoic acid, sorbates or glycol esters. These additives take no part in the active substances required of the preparations that contain them; nevertheless they can be poorly tolerated. Therefore, it is preferable to propose products, in particular in the dermocosmetics field, that do not use such preservative additives, but whose shelf life and microbial cleanliness are adequate. To this end, said products must be sterile. Sterility is defined by standard EN 556 and the European Pharmacopoeia in force as the probability of a microorganism proliferating in said product. Typically, said probability for a sterile product is below $10^{-6}$. The applicant has determined that for products targeted by the invention, sterilization must be performed according to a method with a sterilizing value, F0, equal to 22 minutes. This value F0 gives a time, expressed in minutes, that quantifies the lethal effect of humid heat at 121° C. on viable microorganisms; the method for determining it is defined by the European Pharmacopoeia in force. A product that is sterile according to the definition of the European Pharmacopoeia has been subjected to a sterilization method with a sterilizing value F0 equal to at least 15 minutes. In practice, said method may comprise several cumulative sterilization steps that do not use only humid heat, but whose cumulated lethal effects are equivalent to this value F0.

The lethal effect is measured in relation to a reference germ: sporulated geobacillus stearothermophilus. These bacteria are particularly heat-resistant and heat-tolerant. Thus, the target sterilization effect is that which would have been produced on these germs, in the medium under study, by heat treatment at 121° C. for 22 minutes. The time for this treatment increases exponentially as the temperature decreases, depending on the type of microorganism that the treatment is to destroy. Consequently, the following formula yields the value of F0:

$$F0 = t \cdot 10^{(T-121/z)}$$

where:

t is the treatment time expressed in minutes;

z is a temperature scale and is defined by the heat resistance of the microorganism under consideration. The value of z is defined experimentally with regard to a parameter D. D is a decimal reduction time, which measures the time required at a given temperature, here 121° C., to reduce the concentration of the microorganism under consideration by 90%. D equals one minute for geobacillus stearothermophilus. Thus, z is the temperature variation that changes the value by a factor of 10; for geobacillus stearothermophilus, z equals 10° C.; these factors, D and z, depend on the medium and in particular vary according to the type of emulsion;

T is the treatment temperature.

Thus, a treatment with a sterilizing value equal to 22 is a treatment that is 22 minutes long at 121° C. (394 K), or a treatment that is 36 seconds long at 135° C. (408 K).

Of course, heating in this way, which reduces viscosity of the emulsion's external phase considerably, has a destructive effect on this last, such that heat sterilization treatments are proscribed by experts and the use of additives or other methods is preferred. These other methods, however, also have disadvantages or are not applicable:

sterilization by irradiation is difficult to implement and there are doubts regarding the decay products;

sterilization by filtering membrane is not, in general, suitable for products as viscous as those used in dermocosmetics; in addition, it may retain the internal phases when these are in condensed or solid state. Lastly, it does not support continuous processes or flow-rates compatible with industrial-scale production of the product.

Document EP-B-2032175 describes a sterilization method, called UHT or Ultra High Temperature, which can be adapted to the sterilization of cosmetic products such as those targeted by the invention. The method and the device described in this document use indirect heating of the emulsion, which is conveyed while kept under pressure in heating and cooling baths, through a tube. This tube ensures there is no contact whatsoever between the products and the baths mentioned. This type of method induces a thermal gradient between the product in contact with the walls of the tube and the product at the center of the flow, and also a thermal gradient between the start and end of the transit through the same bath. These characteristics make it difficult to check the lethal value of the sterilization thus performed. Therefore, with this method it is not possible to control strictly the durations of heating, plateauing at high temperature and cooling. In fact, the thinness of said tube makes it difficult to achieve adequate flow-rates, particularly when the product to be sterilized is very viscous and because these durations are controlled by the flow-rate of the product through the tube. In addition, the heating and cooling of the product during its travel into the tube change its viscosity, both along the tube and through its cross section; this makes controlling the pumping of said product complicated and requires the use of high pressures. Furthermore, contact with the hot walls of the tube is likely to affect the quality of the product negatively, whereas contact with said tube's cold walls, in the cooling zone, has a tendency to cause the fatty substances within said product to solidify with no possibility of subsequent re-homogenization. Controlling this method is therefore a delicate matter and the results poorly reproducible. Lastly, this method is not suitable for industrial-scale treatment of high volumes of product, with flow-rates above 1 m³/hour.

Other ultra-high temperature treatment methods known from prior art, in particular by infusion or injection, as applied to food products, are also not very suitable for processing this type of product, and require the contact with steam to be realized when the product is in the liquid phase in order to achieve full effectiveness. Even though the sterilization properties required for food products are less stringent than for the products targeted by the invention and even though the organoleptic properties of food products that are treated using ultra-high temperature sterilization methods are less fragile than the stability of the emulsions targeted by the invention, it is common, according to prior art, to add surfactant additives to said products to strengthen their stability in regard of the sterilization cycle. Thus, documents EP 0524751 and JP 2004 105181 describe methods of sterilizing food emulsions, which food emulsions are stabilized beforehand by adding an ester. This type of surfactant additive is similar to preservatives, which the invention aims to eliminate.

OBJECT AND SUMMARY OF THE INVENTION

To resolve the drawbacks of the prior art, the invention proposes a method for continuous sterilization of emulsions, dermocosmetic preparations in particular, at high temperature; this method comprises the following steps:
a. gradually pre-heating said emulsion up to a pre-heating temperature T1, which is the stability limit of said emulsion;
b. performing ultra-high temperature sterilization by infusion of said emulsion, thus pre-heated, which comprises:
 i. heating up to a sterilization temperature T2;
 ii. plateauing at the sterilization temperature;
 iii. cooling under vacuum at an end-of-sterilization temperature T3;
c. cooling gradually with agitation to a storage temperature T4.

Thus, the method that is the subject of the invention comprises, within the sequence of the process, phases of gradual heating and, above all, of gradual cooling, on either side of the sterilization operation. These gradual heating and cooling phases allow the following:
during heating, to bring the emulsion to a state of fluidity suitable for the infusion sterilization method, without breaking said emulsion;
during cooling, to recover the product characteristics as an emulsion, which were partially degraded during the sterilization operation.

The heating and cooling rates of steps i) and iii) of the sterilization phase are imposed by the infusion method's thermodynamics.

The invention can be implemented according to the advantageous embodiments described below, which may be considered individually or in any technically effective combination.

Advantageously, with the temperatures expressed in degrees Kelvin, temperature T3 is lower than or equal to temperature T1, with the difference between temperature T1 and temperature T3 less than 5K:

$$(T1-5) \leq T3 \leq T1.$$

Thus the emulsion is rid of all the water absorbed during the sterilization by infusion phase but remains at a sufficient temperature, suitable for the subsequent cooling treatment.

Advantageously, cooling step c) is performed in plateaus, with a change in temperature between two plateaus of 15K (15° C.) at most. In this way, respecting this condition avoids any thermal shock during cooling, which could degrade the emulsion.

Advantageously, cooling step c) comprises two plateaus carried out with means comprising a plate heat exchanger. Thus, respecting the plateaus prevents the product coming into contact with walls that are too cold and that would cause the fatty substances to solidify, while allowing a volume of product compatible with industrial-scale applications to be treated.

Advantageously, temperature T2 is 418K (145° C.). This temperature allows a sterilizing value F0=22 to be achieved in a sterilization time of 6 seconds. The sterilization method results inevitably in a dilution of the emulsion. Choosing these treatment conditions returns its initial properties to the emulsion during the cooling phase and is, in addition, suitable for a broad range of dermocosmetic products.

Advantageously, temperature T1 is chosen to be 328K (55° C.). At this temperature, most of the emulsions considered by this invention can be placed in a state of fluidity suitable for passing into the UHT infusion sterilization device without degrading the emulsion.

From a practical point of view, and for industrial application of the method, parameters T1, T2, T3 and the holding time are fixed, irrespective of the product; these correspond to thermodynamic equilibria that allow the rapid sterilization heating and cooling, as well as the recovery of all the water absorbed by the emulsion during this process. The state of the emulsion after these first treatment phases depends on the type of the products that were treated, but the selected parameters ensure that only the homogeneity of the emulsion is affected by the treatment; this homogeneity is restored during the cooling phase; this phase is adjusted as to graduality and agitation for the product in consideration.

To this end, the method that is the subject of the invention comprises advantageously a mechanical treatment step, called mixing, by shearing the emulsion after sterilization step b).

Advantageously also, the method that is the subject of the invention also comprises a mixing step after the cooling step c).

These mixing steps allow the agitation rate of the emulsion necessary to restore its uniformity to be adjusted.

The invention also relates to a device for continuously implementing the method that is the subject of the invention, which device comprises:
x. a UHT infusion sterilization device;
y. plate heat exchangers for pre-heating and cooling the emulsion to be sterilized;

z. mechanical means of treating the emulsion by shearing at the exit from the UHT sterilization device.

Advantageously, the heat exchangers are of the type known as "scraped-surface". In this way, the heat exchangers provide both the heating and cooling of the emulsion, without thermal shock when in contact with the walls; they also provide all or part of the agitation of the emulsion required to reinstate its uniformity.

Advantageously, the device that is the subject of the invention comprises two cooling scraped surface heat exchangers, which correspond to two cooling temperature plateaus. Thus, the first heat exchanger can be set to a temperature sufficiently high to prevent the fatty substances contained in the emulsion from solidifying when in contact with the walls of said exchanger.

According to a particularly advantageous embodiment of the device that is the subject of the invention, the latter comprises a disc-type mixing machine at the outlet from the sterilization device, before the inlet of the first cooling scraped surface exchanger. Thus, said mixing machine can homogenize the emulsion just after its cooling, when it is at a relatively high temperature, of the order of 323 K (50° C.) and stop any beginning of coalescence, creaming or flocculation of said emulsion.

Advantageously, the device that is the subject of the invention comprises a disc-type mixing machine at the outlet from the last cooling heat exchanger. This characteristic, which can be combined with the previous advantageous embodiment, perfects the homogenization of the emulsion to prevent any degradation of said homogeneity during the subsequent operations.

Advantageously, the device that is the subject of the invention comprises, according to its embodiments that include disc-type mixing machines, bypassing means to prevent the emulsion to be sterilized from passing through said disc-type mixing machines. Thus, the cooling cycle and the amount of agitation can be adjusted, depending on the type of emulsion being treated.

The invention also concerns an emulsion for dermocosmetic applications, which emulsion is sterile according to the EN 556 standard and the European Pharmacopoeia, and, more specifically, with a sterility such as achieved for a sterilizing value F0=22. Such an emulsion, because of its level of sterilization, which is out of the reach of the methods known from prior art, has exceptional preservation qualities without the use of preservation additives, which means that its tolerance can be improved and also that active substances that are not compatible with these additives can be used.

BRIEF DESCRIPTION OF THE DRAWINGS

The invention is described below according to various preferred, non-limiting embodiments and with reference to FIGS. 1 to 3 wherein:

FIG. 1 shows a synoptic view of the implementation of a method according to an exemplary embodiment of the invention;

FIG. 2 is an example of a heat cycle and of the correlated change in the viscosity of a product being subjected to a treatment according to an exemplary embodiment of the invention.

DETAILED DESCRIPTION OF THE EMBODIMENTS

Figure 3:
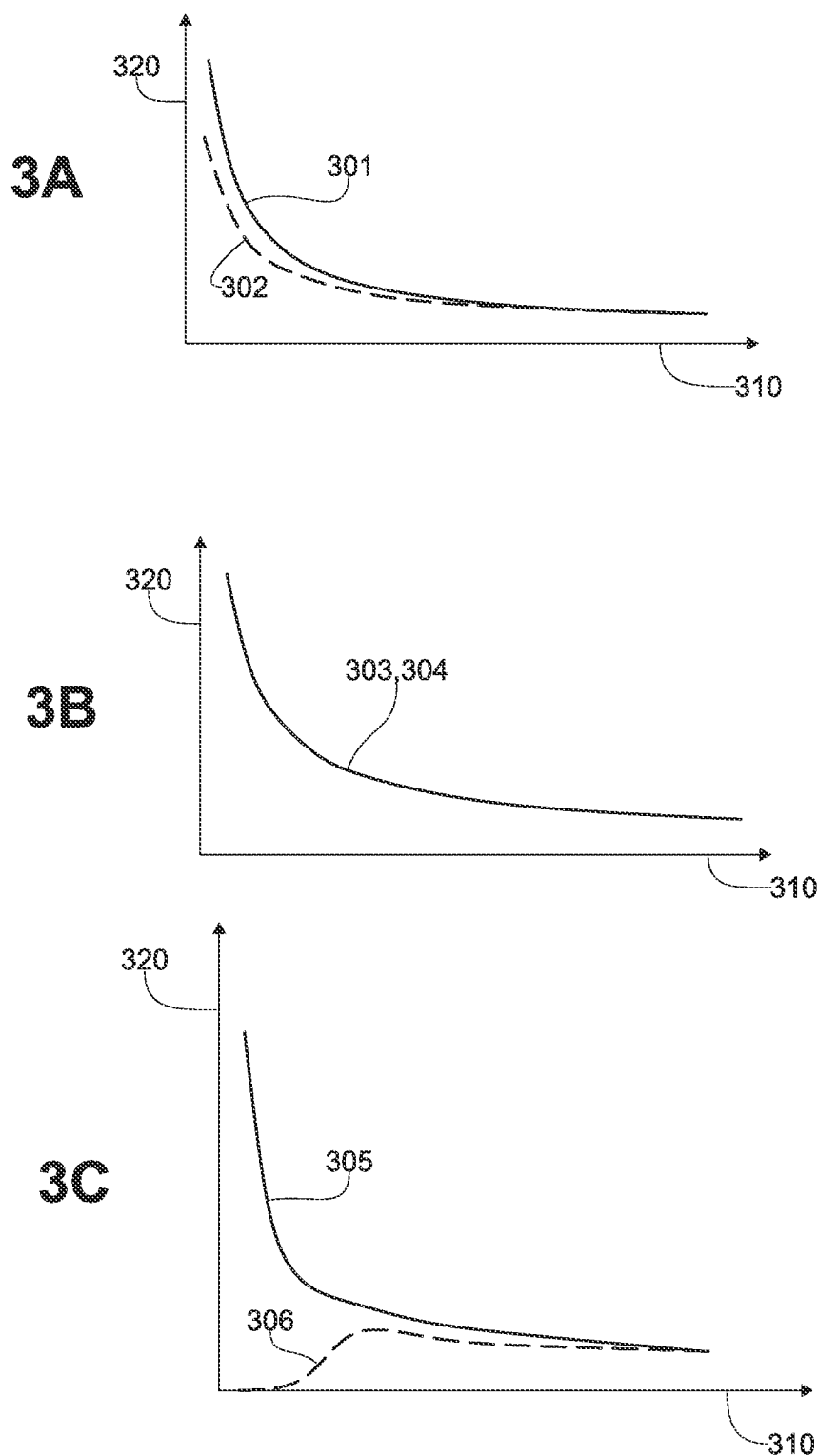
FIG. 3 is an example of the change in viscosity of an emulsion under the effect of temperature to determine the stability limit temperature, FIG. 3A at a temperature below this temperature, FIG. 3B at this temperature and FIG. 3C at a temperature above this stability limit temperature.

FIG. 1: the markers designate the steps in the method as well as the means of implementing this method during said steps. The product to be sterilized is initially stored in the form of an emulsion in a tank (110). The treated products are mainly emulsions with an aqueous external phase and a fatty internal phase. As a non-limiting example, the method that is the subject of the invention is suitable for sterilizing and obtaining a sterile emulsion; said emulsion comprises an aqueous or continuous external phase, which comprises hydrophilic components, in particular a carboxymethyl cellulose gel and an internal phase comprising oily matter and lipophile-modified polyacrylates. The method can nevertheless be applied to emulsions with a fatty continuous phase and an aqueous dispersed phase. The device and method that are the subjects of the invention can be implemented for a wide variety of emulsions, with viscosity ranging from 600 Cps to 45,000 Cps, i.e. for dermocosmetic products ranging from milk to balm.

Such emulsions are obtained by separating and breaking the drops of the internal phase so as to create a uniform dispersion of these in the external phase. This dispersion is obtained by means of a mechanical effect: the mechanical energy thus introduced, e.g. by agitation or injection, into the product is stored in the surface tension of the drops at the interphases. The product is thus uniform when the size of the drops is substantially the same in all the emulsion. From this emulsified state, the emulsion is broken when, by various mechanisms, the internal phase drops agglomerate until they again form two separate phases. In this case, the emulsion can only be formed by reintroducing the mechanical energy, as was done initially. Between the initial emulsion and the broken emulsion, there are intermediate states for which the distribution of the sizes of the drops of the internal phase is not uniform but in which, under defined thermodynamic conditions or with a minimal introduction of mechanical energy, the emulsion can be again homogenized. The method and device that are the subjects of the invention aim to preserve at all times, particularly during the most severe phases of the treatment, the emulsion in a state that makes it possible to achieve its re-homogenization easily. This treatment principle is not known to the sterilization methods of emulsified food products such as milk.

FIG. 2, which gives the temperature (210) and viscosity (230) of the emulsion as a function of time (220) allows the heat cycle (215) to be followed correlatively with the viscosity (235) of the emulsion during the various steps (120, 130, 140, 160) of the method of the invention.

Going back to FIG. 1, pumping means (115) bring the product to be treated towards two scraped surface exchangers (121, 122) to take said product, during a pre-heating step (120) to a temperature (T1), which is at the limit of the emulsion's stability. Temperature T1 is determined by analyzing the change in the emulsion's viscosity as a function of the temperature, as shown in FIG. 3.

FIG. 3: the analysis of the dynamic viscosity (320) of an emulsion depending on its shearing rate (310) is given for increasing shearing rates, or shearing speeds gradients, that are increasing (301, 303, 305) or "outward" curve and for decreasing shearing rates (302, 304, 306) or "return" curve. This analysis, performed by means of a rheometer comprising a moving part (cylinder or cone) shearing the emulsion between the wall of said mobile part and a fixed wall, is performed at different temperatures. Said analysis brings three characteristic behaviors to the fore. According to the example of realization presented in FIG. 3, the shearing rate (310) varies between 10 s$^{-1}$ and 150 s$^{-1}$.

FIG. 3A: for temperatures below temperature T1, the return curve (302) highlights lower viscosity values than the outward curve (301) for a single shearing rate, because the moving part's shaking tends to fluidize the emulsion.

FIG. 3C: for temperatures above T1, the agitation, combined with the outward (305) temperature destroys the emulsion, which is visible on the return curve (306) where viscosity falls.

FIG. 3B: when the test is performed at temperature T1, the viscosity varies according to the outward (303) shearing rate but comes back to the same viscosity after agitation of the moving part on the return (304).

Thus, temperature T1 can be determined by studying the rheological behavior of the emulsion, depending on the temperature.

Going back to FIG. 1, the pre-heating step (120) advantageously uses scraped surface exchangers to provide simultaneously a very gradual and uniform rise in the temperature of the emulsion. Thus, the pre-heating speed is between 0.1° C.·s$^{-1}$ and 1° C.·s$^{-1}$.

The number of exchangers is chosen depending on the required flow-rate, to allow continuous treatment, suitable for industrial use. This flow-rate is in particular greater than 1 m$^3$/hour. Such an exchanger comprises a stator and a rotor fitted with blades. The stator comprises a double wall heated to the desired temperature by fluid circulation, such that the inner wall of the exchanger (121, 122) reaches the set point temperature T1. According to an advantageous exemplary embodiment, temperature T1 is chosen as 328K (55° C.). This temperature allows the required emulsion fluidity to be obtained without degrading it. The rotor blades continuously scrape the inner wall of the exchanger, such that the instantaneous contact time of a volume of emulsion with said wall is shortened; this avoids thermal shocks that can occur when the cold product comes into contact with the hot exchanger wall.

The gradual pre-heating step (120) is followed by the sterilization step (130). Sterilization is performed according to a method called "by infusion". This method consists of pulverizing a jet of the product into an enclosed space filled with water steam at the desired temperature. To perform this pulverization, the emulsion must be practically liquid. Since the exchange surface between the product drops and the steam is very large, heating the product to the sterilization temperature T2 is practically instantaneous in the entire volume of product injected into the sterilization chamber. During this heating, the product absorbs water corresponding to the condensation of the quantity of steam that has transmitted its heat to the product. The product is kept, during a plateauing step (132), at temperature T2, then directed towards a rapid cooling device (133). Advantageously, T2 is chosen as equal to 418K (145° C.), the plateauing time T, during the next step (132) is 6 seconds. These conditions allow a sterilizing value of F0 equal to 22 minutes to be achieved.

Sterilization (130) then proceeds to rapid cooling (133) called "flash". The product, heated to temperature T2, is connected to a chamber (133) that was vacuum-filled by appropriate means (139). The product aspired into this chamber undergoes sudden decompression, which is accompanied by a violent release of steam. The latent vaporization heat removes thermal energy from the product and thus cools it, by tearing droplets away. The thermodynamic cycle is regulated such that the water absorbed during the heating in the first phase (131) of the sterilization cycle is recovered in the form of a condensate during the flash cooling cycle (133). Thus, temperatures T1 and T3 have to be close to each other and the difference between T3 and T1 is adjusted according to the type of product, and according to the resilience and appearance of the emulsion. Since the device that is the subject of the invention must be able to treat different types of products, the treatment temperatures T1, T2 and T3 are optimized so as to fulfill simultaneously all the sterility requirements, through the value of T2 and the plateauing time, depending on the ability to re-homogenize the emulsion after the sterilization treatment, in particular through the choice of T1 and T3. These parameters are then fixed for the types of products to be treated. Thus, the applicant has determined an advantageous temperature T3, equal to 323K (50° C.). Adjustments to the treatment for the specific product are realized during subsequent phases (140, 150).

At the end of the sterilization step (130) and depending on the type of product treated, a homogenization step (140) is realized, for example using a disc-type mixing machine. This step aims to re-homogenize the emulsion quickly and to stop any coalescence phenomenon. Alternatively, a bypass valve (141) allows this homogenization step to be skipped for more stable products.

A gradual cooling step (150), using a plurality of scraped surface exchangers (123, 124), brings the emulsion back to a temperature (T4), close to or slightly higher than the ambient temperature to carry out the storage of the emulsion for later packaging. The cooling speed during this gradual cooling step is between 0.01° C.·s$^{-1}$ and 0.5° C.·s$^{-1}$.

Advantageously, T4 is chosen as 303K (30° C.), since emulsions are very stable at this temperature and sufficiently fluid for easy packaging. This temperature for storing in tanks also prevents emulsion condensation phenomena inside said tank. The number of exchangers in each of these sets is chosen depending on the foreseen flow-rate.

Cooling is realized in several steps, respecting the condition of a maximum interval of 15K (15° C.) between two successive plateaus. This characteristic prevents the fatty drops of the emulsion's internal phase from solidifying when they come in contact with a wall that is too cold. If such solidification were to occur, said drops would become impossible to divide and disperse in the external phase. Thus, starting from T3=323K (50° C.) to finish at T4=303K (30° C.), cooling (150) is performed in at least two steps. Thus, the device that is the subject of the invention comprises at least two exchangers, which correspond to two temperature plateaus. The first scraped surface exchanger (123), or set of exchangers, is set to a temperature T'$_4$, which is just lower than temperature T3. Thus, for a temperature T3 of 323K (50° C.), T'$_4$ is chosen to be equal to 313K (40° C.) and the second exchanger is set to temperature T4=303K (30° C.). Here too, using scraped surface exchangers (123, 124) helps prevent thermal shocks, while providing, for certain products, sufficient agitation to re-homogenize the emulsion. The practical number of exchangers is chosen depending on the flow-rate to be achieved. Thus, two groups of exchangers corresponding to these two plateaus can be installed in parallel or several exchangers corresponding to closer thermal plateaus can be installed in series.

Depending on the type of product treated, a last mixing (145), for example in a disc-type mixing machine, completes the homogenization of the emulsion. Alternatively, for other products, this step may be omitted, with a bypass valve (146)

that connects the outlet of the second thermal exchanger (124) to the sterile buffer tank (160), before the product is packaged.

According to a first exemplary embodiment, the method that is the subject of the invention is suitable for UHT sterilization of a product consisting of an emulsion with an aqueous continuous phase and a fatty internal phase, for example a product comprising:
  water (Aqua),
  a mineral oil such as paraffin oil (paraffinum liquidum),
  glycerin,
  glyceryl stearate,
  squalane,
  a carbomer,
  and triethanolamine.

The method that is the subject of the invention allows this product to be sterilized with a sterilizing value F0 of 22 minutes.

According to a second example of realization, the method that is the subject of the invention is suitable for sterilizing a dermocosmetic product consisting 5%-50% of an oily continuous phase and an aqueous internal phase, for example a product comprising:
  glycerin,
  xanthan gum,
  (Di)Steardimonium Hectorite,
  caprylic/capric triglycerides,
  white beeswax,
  evening primrose oil,
  isopropyl palmitate,
  PEG-30 Dipolyhydroxystearate,
  citric acid monohydrate,
  and water.

The method that is the subject of the invention allows this product to be sterilized with a sterilizing value F0 of 22 minutes.

According to a third example of realization, the method that is the subject of the invention is suitable for UHT sterilization of a dermocosmetic product consisting of a surfactant medium with anionic amphoteric and non-ionic binary or ternary association, for example a product comprising:
  zinc coceth sulfate,
  disodium lauteth sulfosuccinate,
  polysorbate 20,
  Ceteareth-60 myristyl glycol,
  lactic acid,
  sodium hydroxide,
  and water.

The method that is the subject of the invention allows this product to be sterilized with a sterilizing value F0 of 22 minutes.

The description above and the exemplary embodiments show clearly that the invention has achieved the goals it envisages. In particular, it makes it possible to realize in-depth, continuous sterilization treatment of a dermocosmetic product or of a fragile galenic preparation to bring them up to a sterility assurance level that allows said product to be preserved for a long time without adding preservatives.

The invention claimed is:

1. A method for high temperature sterilization of a dermocosmetic preparation, comprising the steps of:
  gradually pre-heating the dermocosmetic preparation in a form of an emulsion up to a pre-heating temperature which is a temperature of said emulsion at a stability limit;
  performing ultra-high temperature sterilization by infusion of said emulsion after it is pre-heated and comprising the steps of:
    heating said emulsion up to a sterilization temperature;
    maintaining said emulsion at the sterilization temperature;
    cooling said emulsion under a vacuum at an end-of-sterilization temperature; and
  gradually cooling said emulsion with agitation to a storage temperature.

2. The method according to claim 1, wherein the end-of-sterilization temperature is lower than or equal to the pre-hating temperature, and a difference between the pre-heating temperature and the end-of-sterilization temperature is less than 5 Kelvin (5K).

3. The method according to claim 1, wherein the step of gradually cooling is performed in plateaus with a maximum change in temperature between two cooling plateaus of 15K or 15° C.

4. The method according to claim 3, wherein the step of gradually cooling utilizes a wall heat exchanger to obtain the two cooling plateaus.

5. The method according to claim 1, wherein the sterilization temperature is 418K or 145° C.

6. The method according to claim 5, wherein the pre-heating temperature is 328K or 55° C.

7. The method according to claim 1, further comprising the step of mechanically processing said emulsion after it is pre-heated by shearing said emulsion.

8. The method according to claim 1, further comprising the step of mixing said emulsion after it is gradually cooled to the storage temperature.

\* \* \* \* \*